US00PP35045P2

(12) United States Plant Patent
Meilland

(10) Patent No.: US PP35,045 P2
(45) Date of Patent: Mar. 21, 2023

(54) BEDDING ROSE PLANT NAMED 'MEIARIBA'

(50) Latin Name: *Rosa hybrida*
Varietal Denomination: MEIARIBA

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/888,764

(22) Filed: Aug. 16, 2022

(30) Foreign Application Priority Data

Aug. 27, 2021 (QZ) ..... PBR 2021/2141

(51) Int. Cl.
*A01H 5/02* (2018.01)
*A01H 6/74* (2018.01)

(52) U.S. Cl.
USPC ..... Plt./150
CPC ..... *A01H 6/749* (2018.05)

(58) Field of Classification Search
USPC ..... Plt./108, 139, 150
CPC ..... A01H 5/0222
See application file for complete search history.

(56) References Cited

U.S. PATENT DOCUMENTS

PP11,836 P2 4/2001 Radler
PP20,175 P2 7/2009 Meilland

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEIARIBA', is disclosed. The new variety forms attractive, single geranium red colored flowers. Attractive glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEIARIBA'.

CROSS REFERENCE TO RELATED APPLCIATIONS

This application claims priority to Plant Breeders' Right Application Number 2021/2141, which was filed at Community Plant Variety Office in the European Union on Aug. 27, 2021, the contents of which are hereby incorporated by reference for all purposes.

STATEMENT REGARDING PRIOR DISCLOSURES BY THE INVENTOR

The first offer for sale of the new variety was Feb. 22, 2021 in France. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of bedding rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) from the cross between the 'MEINOIRAL' variety (not patented) and an unnamed seedling (not patented). The male parent (i.e., the pollen parent) of the new variety was the 'MEIZMEA' variety (U.S. Plant Pat. No. 20,175).

The parentage of the new variety can be summarized as follows:

('MEINOIRAL' x Unnamed Seedling) x 'MEIZMEA'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms geranium red colored flowers, (b) produces single flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent ('MEINOIRAl' x Unnamed Seedling) produces pink colored flowers, whereas the new variety produces geranium red colored flowers. In addition, the 'MEIZMEA' variety (i.e., pollen parent) displays dark pink colored flowers, whereas the new variety displays geranium red colored flowers. Moreover, the new variety can be readily distinguished from other similar non-parental varieties. For example, the 'RADRAZZ' variety (U.S. Plant Pat. No. 11,836) produces semi-double flowers, whereas the new variety produces single flowers.

The new variety has been named 'MEIARIBA'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during August while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—obverse.

Element 8—illustrates a specimen of a fully open flower—plan view—reverse.

Element 9—illustrates a specimen of a fully open flower—plan view—obverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—upper surface.

Element 16—illustrates a specimen of a leaf with 3 leaflets—plan view—under surface.

Element 17—illustrates a specimen of a leaf with 5 leaflets—plan view—under surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during August while budded on their own roots and growing outdoors at Le Cannet des Maures, Var, France.

Botantical classification: *Rosa hybrida* cultivar MEIARIBA.

Commercial classification: Bedding Rose Plant.

Plant:

*Habit.*—Bushy.

*Height.*—Approximately 100 cm on average.

*Width.*—Approximately 100 cm on average.

*Type.*—Floribunda.

Branches:

*Color.*—Young stems: commonly near Yellow-Green Group 146C. — adult wood: commonly near a color between Yellow-Green Group 145A and Yellow-Green Group 145B.

*Length.*—From the crown to the flower is typically between 50 cm to 80 cm.

*Diameter.*—Typically between 0.5 cm to 0.8 cm on average.

*Young shoots.*—Anthocyanin coloration: absent.

*Thorns.*—Configuration on adult stems: rather elongated with the tip very curved downward on the upper surface and concave on the under surface. — long prickles — quantity: commonly 5 thorns per 10 cm long young stem and commonly 10 thorns per 10 cm long adult stem. — long prickles — length: typically between 0.6 cm to 0.7 cm on young stems and typically between 0.6 cm to 1.0 cm on adult stems. — long prickles — width: approximately 0.2 cm on average on young stems and typically between 0.2 cm to 0.3 cm on adult stems. — long prickles — base: shape is obovate; length is approximately 0.6 cm on average on young stems and typically between 0.4 cm to 0.7 cm on adult stems. — long prickles — color on young stems: commonly near Yellow-Green Group 152C more or less covered with near Greyed-Red Group 178A. — long prickles — color on adult stems: commonly near Greyed-Orange Group 177B. — small prickles — quantity: absent.

*Internode.*—Numbers on the entire branch: typically between 10 to 15. — length: typically between 3.0 cm and 4.0 cm.

Foliage:

*General appearance.*—Rather dense, with a glossy aspect.

*Number of leaflets.*—3, 5, 7; most often 7.

7 *leaflets leaf.*—Length: approximately 15.5 cm on average. — width: typically between 6.5 cm to 7.5 cm.

*Terminal leaflet.*—Length: typically between 3.5 cm to 4.5 cm. — width: typically between 2.5 cm to 3.5 cm.

*New foliage.*—Upper surface color: commonly near Green Group 137C more or less covered with near Greyed-Purple Group 187C. — under surface color: commonly near Green Group 138B more or less covered with near Greyed-Purple Group 187D.

*Adult foliage.*—Upper surface color: commonly near Green Group 137A. — under surface color: commonly near Green Group 138B. — anthocyanin coloration: absent.

Leaflets:

*Shape.*—Tip: acuminate. — base: rounded.

*Glossiness of upper surface.*—Strong.

*Texture.*—Upper and under surfaces are leathery.

*General appearance.*—Oval.

*Serration.*—Small and single.

*Undulation on the margin.*—Medium.

*Venation.*—Color is commonly near Green Group 138B and pattern is imparipinnate.

*Petiole rachis.*—Color of upper surface: commonly near Green Group 137A. — color of under surface: commonly near Green Group 138B. — texture: upper surface is little glandular, under surface is very few prickles. — rachis of terminal leaflet: length is typically 4.5 cm to 6.0 cm and diameter is approximately 0.1 cm on average.

*Petioles.*—Upper surface: little glandular. — under surface: very few prickles. — color of upper surface: commonly near Green Group 137A. — color of under surface: commonly near Green Group 138B. — length: typically between 1.3 cm to 2.3 cm. — diameter: approximately 0.1 cm on average.

*Stipules.*—Length: typically between 1.0 cm to 1.5 cm. — width: typically between 0.3 cm to 0.4 cm. — color of upper surface: commonly near Green Group 137B. — color of under surface: commonly near Green Group 137C.

Inflorescence:

*Number of flowers per stem.*—Between 4 and 40 flowers per stem.

*Lastingness of the bloom.*—On the plant: approximately 3 weeks. — in vase: not tested.

*Bud.*—Shape: conical. — size: small. — length: approximately 1.8 cm on average. — width: approximately 1.0 cm on average. — color as calyx breaks: upper surface: commonly near a color between Red Group 53A and Red-Purple Group 59A, basal spot is very little and near Green-White Group 157A. under surface: commonly near Red Group 53A, basal spot is very little and near Green-White Group 157C.

*Sepals.*—Number: commonly 5. — length: typically between 1.8 cm to 2.0 cm. — width: typically between 0.5 cm to 0.6 cm. — shape: at the top: elongated and narrow, at the base: upright. — extensions: absent or very weak elongated extensions on 2 or 3 sepals, which number is between 1 and 4 per sepal; length is typically between 0.3 cm to 0.6 cm, and width is approximately 0.1 cm on average. — upper surface: texture: tomentous. color: commonly near Green Group 138B. — under surface: texture: smooth. color: commonly near Green Group 138A.

*Receptacle.*—Color commonly near Green Group 138B more or less covered with near Greyed-Red Group 178A. — length: approximately 0.6 cm on average. — width: approximately 0.5 cm on average. — surface: smooth. — shape: pitcher shaped.

*Peduncle.*—Length: typically between 1.8 cm to 2.5 cm. — width: approximately 0.15 cm on average. — surface: glandular. — color: commonly near Green Group 138B.

*Flower.*—Diameter when open: approximately 5.5 cm on average. — depth: commonly between 2.0 cm to 2.5 cm. — shape: flat cup shaped. — shape when viewed from above: irregular rounded. — shape of the upper part of the flower profile: flat. — shape of the lower part of the flower profile: flattened convex. — type: single. — number of petals under normal conditions: typically 5 petals. — petals: shape: rounded (rounded at the base and flat at the top). texture: leathery. length: approximately 2.5 cm on average. width: approximately 3.0 cm on average. — undulation of the petal: very strong. — reflexing of the petal: medium. — petal incision: absent or very few. — petal arrangement: imbricated without petaloids. — petal drop: petals drop off cleanly before drying. — fragrance: none. — discoloration of the flower: very weak. — color when opening: basal spot on the upper surface: commonly near White Group 155D. upper surface: commonly near Red-Purple Group 63A suffused with near Red Group 53A. basal spot on the under surface: commonly near White Group 155D. under surface: commonly near Red-Purple Group 63A. — color of the open flower: basal spot on the upper surface: commonly near White Group 155D. upper surface of the flower: commonly near Red-Purple Group 63A suffused with near Red Group 53A. basal spot on the under surface: commonly near White Group 155D. under surface of the flower: commonly near Red-Purple Group 63A. — anthers: number is 80 on average, length is approximately 0.1 cm on average, width is approximately 0.1 cm on average, coloration is commonly near Orange Group 24B, and arrangement is regular around styles. — filaments: length is typically between 0.4 cm and 1.0 cm and coloration is commonly near Greyed-Orange Group 166C. — styles: length is approximately 0.7 cm on average, coloration is commonly Greyed-Purple Group 185A, and number is typically between 20 to 25. — stigmas: length is approximately 0.1 cm on average and coloration is commonly near Greyed-Yellow Group 162A. — pollen: color is commonly near Greyed-Yellow Group 162B, and amount is abundant. — hips: diameter and length is typically between 0.7 cm to 1.0 cm on average, color is commonly near Yellow-Green Group 146B, and shape is rounded.

Development:

*Vegetation.*—Very strong.

*Blooming.*—Early in the season, very abundant and nearly continuous typically from May to the first frosts in France.

*USDA hardiness zone.*—Zone 5 to 9.

*Tolerance to disease.*—Good, and particularly against Black Spot (*Diplocarpon rosae*).

The new 'MEIARIBA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIARIBA' characterized by the following combination of characteristics:

(a) forms geranium red colored flowers, (b) produces single flowers, and (c) exhibits a bushy growth habit;

substantially as herein shown and described.

* * * * *

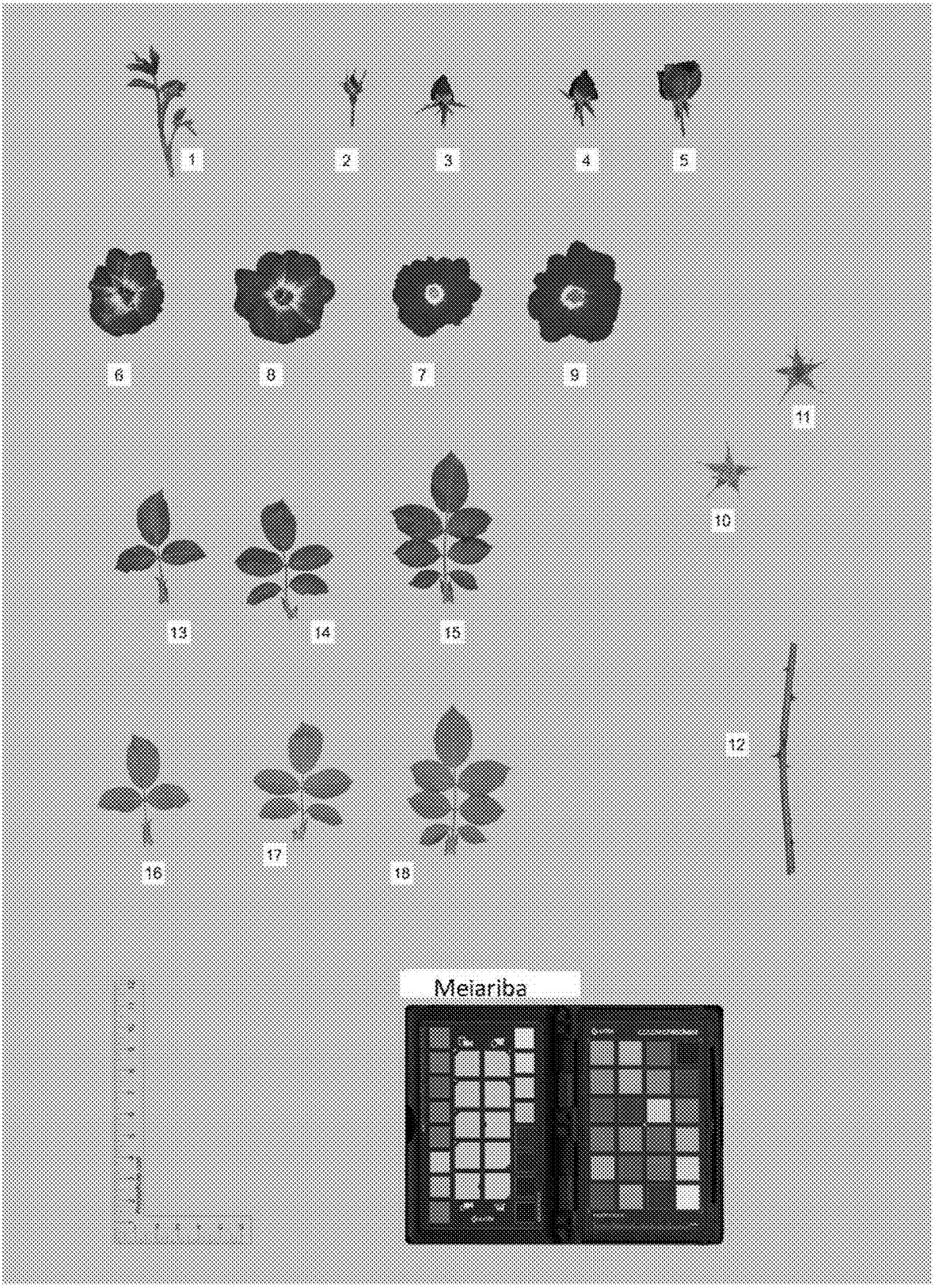
1
2
3
4
5
6
8
7
9
11
10
13
14
15
12
16
17
18
Meiariba